United States Patent [19]

Nimry et al.

[11] 4,393,222

[45] Jul. 12, 1983

[54] TRICYCLO[6.4.0.0²,⁷]
DODECANE-3,6-DIPHENYL-1,8,4,5-TET-
RACARBOXYLIC ACID DIANHYDRIDES

[75] Inventors: Tayseer S. Nimry, Wheaton; Ellis K. Fields, River Forest, both of Ill.

[73] Assignee: Standard Oil Company (Indiana), Chicago, Ill.

[21] Appl. No.: 386,888

[22] Filed: Jun. 10, 1982

Related U.S. Application Data

[62] Division of Ser. No. 294,348, Aug. 19, 1981, Pat. No. 4,358,580.

[51] Int. Cl.³ ............................................. C07D 493/04
[52] U.S. Cl. ....................................................... 549/234
[58] Field of Search ........................................... 549/234

[56] References Cited

U.S. PATENT DOCUMENTS

| | | | |
|---|---|---|---|
| 3,257,418 | 6/1966 | Vermont | 549/234 |
| 3,299,102 | 1/1967 | Bradshaw | 549/234 |
| 3,413,316 | 11/1968 | Bradshaw | 549/234 |
| 3,423,431 | 1/1969 | Starr et al. | 549/234 |
| 3,472,749 | 10/1969 | Bradshaw | 549/234 |
| 3,503,998 | 3/1970 | Schuller et al. | 549/234 |
| 4,360,657 | 11/1962 | Nimry et al. | 549/234 |

*Primary Examiner*—Lester L. Lee
*Attorney, Agent, or Firm*—Gunar J. Blumberg; William T. McClain; William H. Magidson

[57] ABSTRACT

Novel polyimides, copolyimides and molding compositions are prepared from novel dianhydrides such as tricyclo[6.4.0.0²,⁷] dodecane-3,6-diphenyl-1,8,4,5-tetracarboxylic acid dianhydride and tricyclo-[6.4.0.0²,⁷] dodecane-1,8,4,5-tetracarboxylic acid dianhydride. The novel polyimides are useful as engineering plastics. The novel dianhydrides are useful for the preparation of the polyimides. Other dianhydrides can be mixed with our novel dianhydrides to make novel copolyimides useful as engineering plastics.

1 Claim, No Drawings

TRICYCLO[6.4.0.0$^{2,7}$] DODECANE-3,6-DIPHENYL-1,8,4,5-TETRACARBOXYLIC ACID DIANHYDRIDES

This is a division, of application Ser. No. 294,348, filed Aug. 19, 1981 and now U.S. Pat. No. 4,358,580.

BACKGROUND OF THE INVENTION

Field of the Invention

The field of this invention relates to novel dianhydrides such as tricyclo [6.4.0.0$^{2,7}$] dodecane-1,8,4,5-tetracarboxylic acid dianhydride (I) and tricyclo [6.4.0.0$^{2,7}$] dodecane-3,6 diphenyl-1,8,4,5-tetracarboxylic acid dianhydride (II) and novel polyimides prepared from these dianhydrides and diamines. These novel polyimides are useful in preparing molded articles, fibers, laminates and coatings.

Background

British Patent Specification No. 570,858 discloses various processes for making fiber forming polymers. It is clear that neither the novel dianhydrides nor the polyimides prepared therefrom, which are useful as moldings, fibers, laminates and coatings, have been contemplated in the prior art.

The general objective of this invention is to provide novel dianhydrides. A more specific object is to provide novel polyimides and copolyimides based on I, II and diamines. Another object is to provide polyimides based on either I or II and other dianhydrides and diamines or mixtures of diamines.

We have found that novel polyimides can be formed by reacting dianhydrides of the following structure:

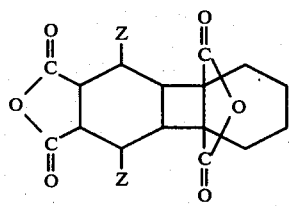

wherein Z is either hydrogen or a benzene radical with diamines. These dianhydrides are prepared by photocycloaddition reactions between 1-cyclohexene-1,2-dicarboxylic anhydride and 3,6-diphenyl-4-cyclohexene 1,2-dicarboxylic anhydride and photocycloaddition reactions between cis-4-cyclohexene-1,2-dicarboxylic anhydride and cis-1-cyclohexene-1,2-dicarboxylic anhydride. Both I and II react readily with a diamine to form a high-molecular-weight polyimide or copolyimide. In the novel process aliphatic, cycloaliphatic, araliphatic and aromatic diamines can be polymerized with I and II in the melt to form high molecular weight polyimides and copolyimides.

Dianhydrides that can be mixed with I or II in a ratio that range from 10:1 to 1:10 as monomers for the synthesis of copolyimides are characterized by the following formula:

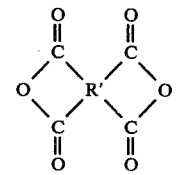

wherein R' is a tetravalent organic radical selected from the group consisting of aromatic, aliphatic, cycloaliphatic, heterocyclic, combination of aromatic and aliphatic, and substituted groups thereof. However, the preferred dianhydrides are those in which the R' groups have at least 6 carbon atoms, wherein the 4 carbonyl groups of the dianhydride are each attached to separate carbon atoms and wherein each pair of carbonyl groups is directly attached to adjacent carbon atoms in the R' group to provide a 5-membered ring as follows:

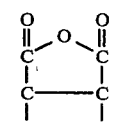

The preferred dianhydrides mixed with either I or II, as recited above, yield upon reaction with the diamines copolyimide structures having outstanding physical properties. Illustrations of dianhydrides in addition to either I or II suitable for use in the present invention include: pyromellitic dianhydride; 2,3,6,7-naphthalene tetracarboxylic dianhydride; 3,3',4,4'-diphenyl tetracarboxylic dianhydride; 1,2,5,6-naphthalene tetracarboxylic dianhydride; 1,2,3,4-cyclopentane tetracarboxylic dianhydride; 2,2',3,3'-diphenyl tetracarboxylic dianhydride; 2,2-bis(3,4-dicarboxyphenyl) propane dianhydride; 2,3,4,5-pyrrolidine tetracarboxylic dianhydride; 3,4,9,10-perylene tetracarboxylic dianhydride; bis(3,4-dicarboxyphenyl) ether dianhydride; ethylene tetracarboxylic dianhydride; 3,3',4,4'-benzophenonetetracarboxylic dianhydride; bis(3,4-dicarboxyphenyl)sulfide dianhydride; bis(3,4-dicarboxyphenyl)sulfone dianhydride; bis(3,4-dicarboxyphenyl)methane dianhydride; 1,4,5,8-naphthalenetetracarboxylic dianhydride; tricyclo [4,2,2,0$^{2,5}$] dec-7-ene-3,4,9,10-tetracarboxylic dianhydride; 3,6-ethenohexahydropyromellitic dianhydride; cyclobutane-1,2,3,4-tetracarboxylic dianhydride; and 1,3-dimethylcyclobutane-1,2,3,4-tetracarboxylic dianhydride; 1,2,3,4-tetramethyl-1,2,3,4-tetracarboxylic dianhydride.

Our process for the manufacture of the novel polyimides comprises reacting about equal molar amounts of the dianhydride with a primary diamine or a mixture of primary diamines. The molecular ratio of the dianhydride to the primary diamine may be in the range of 1.2 to 1 preferably in the range of 1 to 1. In suitable method, the reaction is conducted as a batch reaction at a temperature of about 130° C. to 300° C. for a period of about 2 to 8 hours in a nitrogen containing organic polar solvent such as N-methyl-2-pyrrolidinone, N,N-dimethylacetamide or pyridine. The polycondensation can also be carried out as a continuous process. The polycondensation can suitably be carried out at a temperature of 130° C. to 300° C., preferably at a temperature of 180° C. to 250° C. The novel polyimides of this invention have the following recurring structure wherein R is a divalent aliphatic or aromatic hydrocarbon radical and Z is a hydrogen or benzene radical:

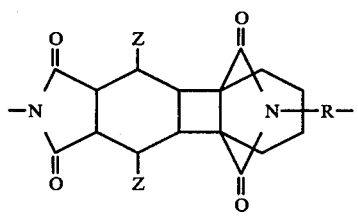

The radical R may be divalent aliphatic hydrocarbons of 2 to 18 carbon atoms or an aromatic hydrocarbon from 6 to 20 carbon atoms, or an aromatic hydrocarbon radical containing from 6 to 10 carbon atoms joined directly or by stable linkage comprising

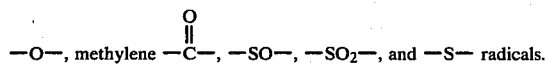

The radical R is derived from aliphatic, araliphatic or cycloaliphatic diamines such as ethylenediamine, propylenediamine, 2,2-dimethylpropylene diamine, tetramethylene diamine, hexamethylene diamine, octamethylene diamine, nonamethylene diamine, decamethylene diamine, dodecamethylene diamine, 4,4'-diaminodicyclohexylethane, xylylene diamine and bis (aminomethyl) cyclohexane. Suitable aromatic diamines useful in Applicant's process include para- and meta-phenylenediamine, 4,4'-oxydianiline, thiobis (aniline), sulfonylbis (aniline), diaminobenzophenone, methylene-bis (aniline), benzidine, 1,5-diaminonaphthalene, oxybis (2-methylaniline), thiobis (2-methylaniline), and the like. Examples of other useful aromatic primary diamines are set out in U.S. Pat. No. 3,494,890 (1970) and U.S. Pat. No. 4,016,140 (1972) both incorporated herein by reference. The preferred diamines are hexamethylene diamine, dodecamethylene diamine and 4,4'-oxydianiline.

In some cases the polyimide may be further polymerized under "solid state polymerization" conditions. The term solid state polymerization refers to chain extensions of polymer particles under conditions where the polymer particles retain their solid form and do not become a fluid mass. The solid state polymerization can be carried out below the melting point of the polyimide and can be conducted in several ways. However all techniques require heating the ground or pelletized polyimide below the melting point of the polyimide, generally at a temperature of about 175° to 300° C. while either sparging with an inert gas such as nitrogen or operating under vacuum. In cases where the polyimides have a low melt temperature, they can be polymerized in the melt under vacuum in thin sections or using thin film reactors known in the art.

Injection molding of the novel polyimide is accompanied by injecting the polyimide into a mold maintained at a temperature of about 25° C. to 150° C. In this process a 20 second to 1 minute cycle is used with a barrel temperature of about 125° C. to 350° C. The latter will vary depending on the Tg of the polymer being molded.

The novel polyimides have excellent mechanical and thermal properties and can readily be molded into useful articles or formed into fibers, films, laminates or coatings. Infrared spectra of the polyimides have confirmed the polyimide structure. Glass transition temperature Tg of the polyimide varied with the particular diamine used as shown in the Examples. Values range from a Tg of 70° C. to 180° C.

Diamines with the amino groups attached directly to the aromatic ring are suitably polymerized with I or II by solution condensation in organic polar solvents. We have found that the polyimides and copolyimides of this invention are improved by the addition of reinforcing material. Suitably about 25 to 60 percent by weight glass fibers, glass beads or graphite or mixtures of these can be incorporated into the polyimides and copolyimides. Any standard commercial grade fibers, especially glass fibers may be used. Glass beads ranging from 5 mm to 50 mm in diameter may also be used as reinforcing material. Injection molding of the novel glass-filled polyimide is accomplished by injecting the polyimide into a mold maintained at a temperature of about 50° C. to 150° C. In this process a 25 to 28 second cycle is used with a barrel temperature of about 125° to 350° C. The injection molding conditions are given in Table I.

TABLE I

| | |
|---|---|
| Mold Temperature | 50 to 150° C. |
| Injection Pressure | 15,000 to 19,000 psi and held for 1 to 3 seconds |
| Back Pressure | 100 to 220 psi |
| Cycle Time | 25 to 28 seconds |
| Extruder: | |
| Nozzle Temperature | 125° C. to 350° C. |
| Barrels: | |
| Front heated to | 125° C. to 350° C. |
| Screw: | |
| 20 to 25 revolutions/minute | |

The following examples illustrate the preferred embodiment of the invention. It will be understood that the examples are for illustrative purposes only and do not purport to be wholly definitive with respect to conditions or scope of the invention.

EXAMPLE 1

Synthesis of Tricyclo[6.4.0.0$^{2,7}$]Dodecane-1,8,4,5-tetracarboxylic Acid Dianhydride (I)

I is a derivative of perhydrobiphenylene. It has the following formula:

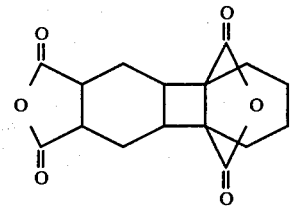

It is prepared from the two related anhydrides, 1-cyclohexene-1,2-dicarboxylic anhydride (III) and its isomer, cis-4-cyclohexene-1,2-dicarboxylic anhydride (IV) in a photocycloaddition reaction.

In a one liter pyrex Erlenmeyer flask, 30.0 g (0.197 mol) of III and 30.0 g (0.197 mol) of IV were dissolved in 350 ml toluene. To this solution approximately 1 g of benzophenone was added. The flask was fitted with a condenser and the solution was irradiated with light from a General Electric (GE) sunlamp. After 18 h, the first crop, 15.2 g, of the product I was isolated. The filtrate was exposed further to light for another 18 h, and 12.0 g of the dianhydride was recovered. At the end of 5 days 60% of the theoretical yield of I was obtained. The new compound melts at 272°-4° C., and decomposes above 290° C. with gas evolution. Analysis: Calcd. for $C_{16}H_{16}O_6$: C, 63.2%; H, 5.3%. Found: C, 63.3%; H, 5.4%.

Mass spectral analysis is consistent with the proposed configuration of I. A molecular ion at 304 was detected. The spectrum also showed two intense peaks at 260 ($I-CO_2$) and 232 ($I-CO_2-CO$).

EXAMPLE 2

Synthesis of Tricyclo[6.4.0.0$^{2,7}$]Dodecane-3,6-Diphenyl-1,8,4,5-Tetracarboxylic Acid Dianhydride (II).

II of the following structure:

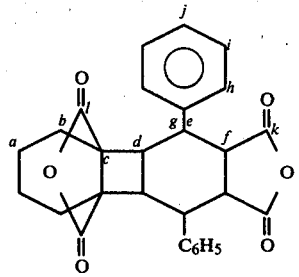

is prepared by the photocycloaddition of 1-cyclohexene-1,2-dicarboxylic anhydride (III) to 3,6-diphenyl-4-cyclohexene-1,2-dicarboxylic anhydride (V). To a one liter pyrex Erlenmeyer flask equipped with a condenser was added 15.2 g (0.1 mol) of (III), 30.4 g (0.1 mol) of (V), and 1.0 g of benzophenone. The mixture was dissolved in 600 ml acetone that was dried over 4 Å molecular sieve, then irradiated with light from a GE sunlamp. Crops of II were filtered off at approximately 18 h intervals. A yield of 70% was obtained after 72 h; mp, 360°-5° C. (dec). Analysis: Calcd. for $C_{28}H_{24}O_6$: C,73.68; H,5.26. Found: C,73.51; H,5.39. The $^{13}$C nuclear magnetic resonance spectrum is consistent with the proposed formulation for II.

| C atom | $^{13}C_{\delta tms}$ | C atom | $^{13}C_{\delta tms}$ |
|---|---|---|---|
| a | 18.7 ppm | g | 137.2 |
| b | 27.3 | h | 128.1 |
| c | 48.8 | i | 127.9 |
| d | — | j | 126.9 |
| e | 37.7 | k | 171.0 |
| f | 46.9 | l | 173.2 |

EXAMPLE 3

Dianhydride I was crystallized from acetone and dried at 120° C. for 18 h. Dodecamethylene diamine (DDA) was distilled under vacuum. DDA, 2.0 g (0.01 mol) was placed in the reaction flask and dissolved in 30 ml of N-methyl-2-pyrrolidinone (NMP) while purging with nitrogen. Compound I, 3.04 g (0.01 mol) was then added all at once and the addition funnel was washed into the flask with another 15 ml of NMP. The mixture was stirred at 25° C. for 1 h, 100° C. for 1 h, and 150° C. for 1 h. At this temperature, 20 ml of NMP were distilled off with most of the water byproduct. The solution which at this point became viscous was heated at 250° C. for 3 h. After cooling to 25° C. the polymer solution was mixed with water in a blender. The polyimide was filtered, washed with water and dried in a vacuum oven at 150° C. for 20 h. Nitrogen Analysis: Calcd. for $C_{28}H_{40}N_2O_4$: 6.0%. Found: 5.8%.

Measurement of the inherent viscosity (I.V.) for this polymer and all polymers in the following examples was carried out on a solution made by dissolving 0.1 g of the polymer in 25 ml of a 60/40 mixture of phenol/tetrachloroethane at 130° C. then cooling to 30° C., the temperature at which the measurement was made. I.V. for the polyimide of Example 3 was 0.74.

The glass transition temperature (Tg) was determined to be 74° C.

EXAMPLE 4

The procedure of Example 3 was employed by using 3.04 g (0.01 mol) of I and 1.16 g (0.01 mol) of hexamethylene diamine (HMDA). The volume of the solvent NMP was 38 ml. Nitrogen Analysis: Calcd. for $C_{22}H_{28}N_2O_4$:7.3%. Found: 8.0%

The polyimide had an I.V. of 0.40 and cast a flexible film by spreading the polymer solution on a glass plate and drying under nitrogen at 120° C. for 1 h. A molded specimen of the polyimide had a Tg of 115° C.; tensile strength, 10,890 psi; ultimate tensile strength, 12,040 psi, and % elongation, 7%.

EXAMPLE 5

I, 3.04 g (0.01 mol), was reacted with 4,4'-oxydianiline (ODA), 2.0 g (0.01 mol), in 45 ml of NMP as in the procedure of Example 3. Nitrogen Analysis: Calcd. for $C_{28}H_{24}N_2O_5$: 6.0%. Found: 5.8%.

The polyimide formed was a flexible film. It had an I.V of 0.29.

EXAMPLE 6

A sealed tube reaction was carried out between I and DDA. Thus, I (0.02 mol) was mixed with a slight excess of DDA (0.021 mol) and placed in a polymer tube. The tube was evacuated and sealed. It was immersed in an oil bath and heated at 100° C. for 2 h. The oil bath temperature was raised to 150° C. After heating at this temperature for 1 h, the seal was broken and the tube was connected to a vacuum pump and heated at 200° C. for 2 h and at 250° C. for an additional 1.5 h. After cooling gradually to room temperature, tough plugs were obtained. Nitrogen content was found to be 5.8%.

I.V. for this polyimide was 0.35 and its Tg was 70° C.

EXAMPLE 7

The reaction between 0.02 mol of I and 0.021 mol of HMDA was carried out as in Example 6. Nitrogen content was 6.9%.

The I.V. for this polyimide was 0.30 and its Tg was 137° C.

EXAMPLE 8

The polycondensation of II with DDA was carried out according to the procedure described in Example 3. II, 3.7 g (0.008 mol), was reacted with DDA, 1.6 g (0.008 mol), in 50 ml NMP. Nitrogen Analysis: Calcd. for $C_{40}H_{48}N_2O_4$:4.5%. Found: 5.1%.

The I.V. of the polyimide was 0.44. A molded specimen had a Tg of 112° C.; ultimate tensile strength, 6240 psi; and % elongation, 7.

EXAMPLE 9

Using 3.7 g (0.008 mol) of II and 0.93 g (0.008 mol) of HMDA in 45 ml of NMP a polyimide was prepared by following the method of Example 3. Nitrogen Analysis: Calcd. for $C_{34}H_{36}N_2O_4$: 5.2%. Found: 5.3%.

The polyimide had an I.V. of 0.32. A molded specimen had a Tg of 177° C.; ultimate tensile strength, 6920 psi; and % elongation, 8.

EXAMPLE 10

II, 5.7 g (0.0125 mol), was reacted with 1.45 g (0.0125 mol) of HMDA in a solvent mixture containing 40 ml NMP and 10 ml xylenes. The reaction flask was fitted with a Dean-Stark trap. After adding the solid dianhydride all at once to the diamine solution that was maintained at 50° C., the mixture was heated at 200° C. for 3 h. The solution was cooled to room temperature then mixed with water in a blender. The polyimide that was produced had a nitrogen content of 5.0% and an I.V. of 0.82.

We claim:

1. As a composition of matter the dianhydrides of the following structure:

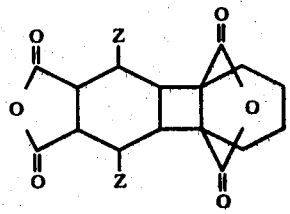

wherein Z is either hydrogen or benzene radical.

* * * * *